United States Patent [19]

Kettman et al.

[11] Patent Number: 4,740,467
[45] Date of Patent: Apr. 26, 1988

[54] METHODS FOR DIAGNOSING SYPHILIS

[75] Inventors: John R. Kettman, Carrollton; Michael V. Norgard, Plano, both of Tex.

[73] Assignee: Board of Regents, The University of Texas, Austin, Tex.

[21] Appl. No.: 702,327

[22] Filed: Feb. 15, 1985

Related U.S. Application Data

[63] Continuation-in-part of Ser. No. 381,929, May 26, 1982, Pat. No. 4,514,498.

[51] Int. Cl.$^4$ .................. G01N 53/00; G01N 33/511; G01N 33/53
[52] U.S. Cl. ......................... 435/7; 436/511; 436/548
[58] Field of Search ............... 435/7; 424/92, 89, 87; 436/548, 545, 546, 511, 597, 533

[56] References Cited

U.S. PATENT DOCUMENTS

4,645,737 2/1987 Coates et al. ........................... 435/7

OTHER PUBLICATIONS

Parish et al., "Identification of an Antigen Specific to Trypanosoma Congolense by Using Monoclonal Antibodies," J. Immunol., 134:593 (1985).
Horejsi et al., "Nitrocellulose Membrane as an Antigen or Antibody Carrier for Screening Hybridoma Cultures," J. Immuno. Methods, 62:325 (1983).
EP-A2-0 095 346, entitled "Hybrid Cell Lines Producing Monoclonal Antibodies Directed Against Treponema", (European publication).
EP-A2-0 140 689, entitled "Hybrid Cell Lines Producing Monoclonal Antibodies Directed Against Treponemal and Use Thereof for Immuno-diagnosis of Treponemal Infections", (European publication).
Lukehart et al., "Characterization of Monoclonal Antibodies to Treponema Pallidum," J. Immunol. 134:585 (1985).
Robertson et al., Infection and Immunity 36:1076–1085 (1982), "Murine Monoclonal Antibodies Specific for Virulent Treponema Pallidum (Nichols)."
Petersen et al., Infection and Immunity, 35:974–978 (1982), "Purification of a Reiter Treponemal Protein Antigen that is Immunologically Related to an Antigen in Treponema Pallidum."
Sau-Ping Kwan et al., Genetic Engineering, 2:31–46 (1980), "Production of Monoclonal Antibodies."
Michael V. Norgard et al., "Sensitivity and Specificity of Monoclonal Antibodies Directed Against Antigenic Determinants of Treponema Pallidum Nichols in the Diagnosis of Syphilis," J. Clin. Microbiol., 20:711–717 (Oct. 1984).
Susan A. Jones et al., "Monoclonal Antibody with Hemagglutination, Immobilization, and Neutralization Activities Defines an Immunodominant 47,000 Mol Wt, Surface-Exposed Immunogen of Treponema Pallidum (Nichols)," *J. Exp. Med.*, 160:1404–1420 (Nov., 1984).
Stella M. Robertson et al., "Murine Monoclonal Antibodies Specific for Virulent Treponema Pallidum (Nichols), "*Infection Imm.* 36:1076–1085 (Jun. 1982).
Kevin S. Marchito et al., "Monoclonal Antibody Analysis of Specific Antigenic Similarities Among Pathogenic *Treponema Pallidum* Subspecies," *Infection Imm.* 45:660–666 (Sep., 1984).
Kevin S. Marchito et al., "Characterization of Surface Associated Antigens of Virulent Subspecies of *Treponema Pallidum* Using Monoclonal Antibodies," *Abst. Fed. Proc.*, B182 (1984).
Susan A. Jones et al., "A Monoclonal Antibody Directed Against a 47,000d Surface Antigen of *Treponema Pallidum* has MHA-TP, TPI, and Complement-Mediated Neutralizing Activity," *Abst. Fed. Proc.*, B173 (1984).
Robert R. Tight et al., "Quantitative Microhaemagglutination Assay for *Treponema Pallidum* Antibodies In Experimental Syphilis," *Br. J. Vener. Dis.* 56:291–296 (1980).
Harold W. Jaffe et al., "Tests for Treponemal Antibody in CSF," *Arch. Intern. Med.* 138:252–255 (Feb., 1978).
James N. Miller, "Value and Limitations of Nontreponemal and Treponemal Tests in the Laboratory Diagnosis of Syphilis," *Clin. Obstet. Gyn.* 18:191–201 (Mar. 1975).
Douglas S. Kellogg, "The Detection of *Treponema Pallidum*, By a Rapid, Direct Fluorescent Antibody Darkfield (DFATP) Procedure, " *Health Lab. Sci.* 7:34–40 (Jan. 1970).
Robert W. Thornburg et al., "A Comparison of Major Protein Antigens and Protein Profiles of *Treponema Pallidum* and *Treponema Pertenue*," *Infection Imm.* 42:623–627 (Nov. 1983), (See also U.S. Ser. No. 545,897 filed Oct. 27, 1983).
James M. Saunders et al., "Developement of Monoclonal Antibodies that Recognize *Treponema Pallidum*," *Infection Imm.* 41:844–847 (Aug. 1983).
Jan D. Van Embden et al., "Molecular Cloning and Expression of *Treponema Pallidum* DNA in *Escherichia Coli* K-12," *Infection Imm.* 42:187–196 (Oct. 1983).

*Primary Examiner*—Blondel Hazel
*Attorney, Agent, or Firm*—Arnold, White & Durkee

[57] ABSTRACT

Murine anti-*Treponema pallidum* monoclonal antibodies were employed in the detection of low numbers of pathogenic treponemes. Monoclonal antibodies were used as a primary antibody source in a solid-phase immunoblot assay system. All monoclonal antibodies assayed were capable of detecting ca. $1.0 \times 10^3$ to $2.5 \times 10^3$ treponemes. Of 13 monoclonal antibodies examined, 3 were able to detect $10^3$ virulent treponemes, and 1 of these antibodies was able to reveal the presence of as few as 500 organisms. Western blot analyses showed that all anti-*T. pallidum* monoclonal antibodies exhibiting high sensitivities for the detection of *T. pallidum* cells were directed against an abundant, 47,000–48,000 dalton surface-exposed antigen of the organism. With two possible exceptions, the monoclonal antibodies tested reacted specifically with *T. pallidum*, either purified or found within a high-contaminating tissue background, and not with *Treponema phagedenis* biotype Reiter, *Haemophilus ducreyi*, *Neisseria gonorrhoeae*, herpes simplex virus type 2, or normal rabbit testicular tissue.

13 Claims, No Drawings

METHODS FOR DIAGNOSING SYPHILIS

The Government may have rights in this invention pursuant to National Institutes of Health Grant Nos. AI16682, AI11851 and CA-23115 awarded by the Department of Health and Human Services.

BACKGROUND OF THE INVENTION

The present application is a continuation-in-part application of co-pending United States patent application Ser. No. 381,929 filed May 26, 1982, now issued as U.S. Pat. No. 4,514,498 dated Apr. 30, 1985.

The present invention relates to methods of diagnosing syphilis and, in particular, to methods of diagnosing syphilis using monoclonal antibodies specific for Treponema bacterial pathogens.

Untreated syphilis in man is a severe, chronic, and very complex disease that can often be extremely difficult to diagnose. Limitations with current diagnostic tools and the absence of a vaccine have allowed syphilis to flourish at the estimated frequency of approximately 350,000 cases per year in the United States alone, even with the availability of effective penicillin treatment.

At present, in the diagnosis of early syphilis, dark-field microscopy is used to identify *Treponema pallidum* in lesion exudates. This method is based upon the observance of characteristic spirochetal morphology and motility. The clinical diversity of early syphilitic lesions, their similarity to those which may occur among patients with other genital ulcer diseases, and the lack or inconclusive nature of serological reactivity which may be present during the primary stage of infection point to the significance assigned to this technique in diagnosis. Further, the results of dark-field microscopy in these circumstances determine the need for treatment and epidemiological follow-up. It is unfortunate that this procedure is fraught with severe biological and technical restrictions which may result in diagnostic errors, inappropriate therapy, misdirection of epidemiological investigation, and the placement of unnecessary stigma upon the patient.

The potential presence of host-indigenous, nonpathogenic treponemes in the oral cavity, genitalia, and gastrointestinal tract with morphology and motility similar to *T. pallidum* precludes an unequivocal identification by dark-field microscopy. In addition, the relatively rapid loss of motility in the presence of atmospheric oxygen necessitates rapid examination of slide preparations to ensure observance of the typical pathogen. This lability reduces the chances for accurate identification of the organism in the exudate.

Furthermore, the potential presence of few treponemes in early lesions may result in a negative dark-field examination despite the presence of the organism. This lack of sensitivity is not surprising. Dark-field examination of *T. pallidum* suspensions containing $10^3$ organisms per ml of exudate is equivalent to 1 organism in 1,000 high dry fields when utilizing a calibrated microscope and therefore would not be readily detectable. Moreover, when Treponema organisms are infrequent, the detection of a single spirochetal organism is a statistically significant event, but this would still be an insignificant result from the point of view of a reliable clinical test.

The limitations of the technique are further compounded by the considerable training, experience and expertise required for the proper use of the dark-field microscope. As a result of these complexities, dark-field examination is either not done or often performed incorrectly. The World Health Organization Scientific Group on Treponemal Infections has recognized this diagnostic void and has stated: "The greatest need is to improve the capability of health care units to identify treponemes." (*W.H.O. Technical Report Series* No. 674, p. 26 [1982].)

The rapid, direct, fluorescent antibody dark-field (DFA-TP) technique proposed by Kellogg, *Health Laboratory Science* 7:34-41(1970), seemed to offer promise as a more efficient method than the dark-field microscopic procedure. However, careful analysis of the data indicated a lack of sensitivity, specificity, and reproducibility in comparison with dark-field examination when polyclonal antibody was utilized as a primary fluorescenated-antibody conjugate.

The diagnosis of asymptomatic and symptomatic neurosyphilis also represents a serious enigma. Again, the similarity of clinical manifestations to those which occur among patients with other diseases of the central nervous system, the inability to detect *T. pallidum* in cerebrospinal fluid of patients, and the lack of sensitive or specific nontreponemal and treponemal serological tests for detecting antibody in cerebrospinal fluid contribute to the inaccuracies of differential diagnosis.

The production of murine monoclonal antibodies that react specifically with *T. pallidum* antigenic determinants and not with the host-indigenous, nonpathogenic *Treponema phagedenis* biotype Reiter or rabbit host testicular tissue antigens has been previously described in Applicants' copending patent application Ser. No. 381,929, filed May 26, 1982, now issued as U.S. Pat. No. 4,514,498. This work offers meaningful new avenues of approach to the development of one or more procedures which satisfy the criteria of rapidity, simplicity, cost effectiveness, high sensitivity, high specificity, and reproducibility for identification of *T. pallidum* or its constituent antigens in lesion exudates or cerebrospinal fluid of patients with early syphilis and neurosyphilis, respectively. Monoclonal antibodies also may be useful in the diagnosis of congenital syphilis in neonates.

This application describes the capability of several anti-*T. pallidum* specific monoclonal antibodies for detecting very low numbers of pathogenic treponemes without interacting with the etiological agents of other sexually transmitted diseases which manifest clinically as genital ulcers.

SUMMARY OF THE INVENTION

In accordance with the present invention a method for diagnosing syphilis and other trepomematoses infections such as yaws and pinta is provided. The method involves admixing a biological sample, such as lesion exudate, cerebrospinal fluid, serum, urine, amniotic fluid, synovial fluid or tissue homogenate from a person suspected of having syphilis, yaws or pinta together with a reagent of monoclonal antibodies which are specific for antigens of virulent subspecies of *Treponema pallidum*, including *pertenue, endemicum, carateum* and *pallidum*. If *Treponema pallidum*, the causative organism of syphilis, is present, an immunological specific binding reaction will occur between the monoclonal antibodies and antigenic sites on the *T. pallidum*. A positive immunoreaction can be detected by a variety of techniques including but not limited to radioimmunoassay, fluorescent immunoassay, enzyme linked immunosorbent assay, agglutination reactions, and complement consumption tests as direct tests as well as a host of other procedures to detect binding of the mouse monoclonal Ig to Treponema as a secondary assay of the primary immunological reaction.

DETAILED DESCRIPTION OF PREFERRED EMBODIMENTS

The following discussion is in terms of the preferred embodiments of this invention, which represent the best mode known to the Applicants at the time of this application.

MATERIALS AND METHODS

A. Bacterial and viral strains and antigens

The virulent Nichols strain of *T. pallidum* was used as the representative pathogen in this study. It was maintained, cultivated, and isolated from the testicles of infected rabbits as previously described in Applicants' co-pending application Ser. No. 381,929, the complete specification of which is herein incorporated by reference. *T. phagedenis* biotype Reiter (Reiter treponeme) was used as a representative saprophytic nonpathogenic treponeme and was cultivated and prepared as described previously in Applicants' prior application Ser. No. 381,929. A suspension of *Haemophilus ducreyi* in sterile skim milk was provided by Eric Hansen, The University of Texas Health Science Center at Dallas. *Neisseria gonorrhoeae* isolated from a patient at the Sexually Transmitted Diseases Clinic of Dallas City and County Public Health Department was provided by Gary Cartwright and was maintained on Thayer-Martin medium. *N. gonorrhoeae* cells were suspended in phosphate-buffered saline (PBS). Herpes simplex virus type 2 (strain 186) in skim milk was a gift of Robin Robinson.

An extract of normal rabbit testicles was used as a source of normal rabbit testicular antigens (containing both tissue and serum antigens) for control tests. Testicles were minced and extracted in serum-saline medium as previously described for *T. pallidum* in Applicants' prior application Ser. No. 381,929 but centrifuged only once for 7 min. at 250×g, yielding a turbid supernatant. Protein assays indicated that 10 ul of this preparation contained about 120 ug of total rabbit protein and that 50% of this total protein was due to the normal rabbit serum in the serum-saline extraction medium. Preparations stored for up to 6 months at −20° C. appeared to possess similar antigenic reactivities, as determined by radioimmunoassay.

Fresh suspensions of *T. pallidum* cells were serially diluted in PBS with siliconized-glass test tubes treated with 2% dichlorodimethylsilane in toluene in an attempt to reduce the quantities of treponemes lost through glass adherence. A starting stock suspension of intact *T. pallidum* cells was quantitated by dark-field microscopy and a 1 ul portion of this and respective dilutions was spotted onto filter paper for use in the immunoblot assay.

B. Monoclonal Antibodies

The production, maintenance and characterization of the monoclonal antibodies directed against *T. pallidum*, as well as pertinent tissue culture methods have been described previously in Applicants' prior application Ser. No. 381,929, filed May 26, 1982, now issued as U.S. Pat. No. 4,514,498 dated Apr. 30, 1985, herein incorporated by reference. Specifically described therein are the monoclonal antibodies herein designated 3G5; 4H7; 13C6; 13G10; 1F4; 3B5; 8G2; 9B12; 4A10-1; 4A10-7; 5A3-2; 13C8; and 11E3.

C. Serological Tests for Syphilis Used to Characterize anti-*T. pallidum* Monoclonal Antibodies Mouse anti-*T. pallidum* monoclonal antibodies, either affinity purified or found within hybridoma clone supernatants were tested for their ability to immobilize *T. pallidum* Nichols in the *T. pallidum* immobilization (TPI) test. The TPI assay was carried out with minor modifications, as previously described in Center for Disease Control, 1964, Manual of Tests for Syphilis, Center for Disease Control laboratory manual, U. S. Department of Health, Education and Welfare, Public Health Service Center for Disease Control, Atlanta. Where necessary, penicillinase (BBL Microbiology Systems, Cockeysville, Md.) was incorporated into the test procedure to eliminate the possibility of residual penicillin in the hybridoma clone supernatants.

The microhemagglutination assay for *T. pallidum* antibodies (Sera-Tek; Ames Division, Miles Laboratories, Inc., Elkhart, Ind.) was performed on both hybridoma clone supernatants and protein A-Sepharose affinity-purified anti-*T. pallidum* monoclonal antibodies by the methods described by the manufacturer.

D. Solid-phase Immunoblot Assays

A modification of the colony blot radioimmunoassay, orginally derived from modifications of procedures described by Henning et al., Radioimmunological Screening Method for Specific Membrane Proteins, *Anal. Biochem.* 97: 153-157(1979); and Raetz, Isolation of *Escherichia coli* Mutants Defective in Enzymes of Membrane Lipid Biosynthesis, *Proc. Natl. Acad. Sci. U.S.A.* 72:2274-2278 (1975) was used to assess the reactivity of anti-*T. pallidum* monoclonal antibodies against various antigens.

In the immunoblot assay, 1 ul of each of the following antigen preparations was spotted onto Whatman no. 42 filter paper strips: *T. pallidum* Nichols, $1 \times 10^8$ to $5 \times 10^8$ cells per ml (quantitated by dark-field microscopy) in PBS: *T. pallidum* Nichols harvested from minced primary chancre lesions of experimental rabbits, $1 \times 10^7$ cells per ml: *T. phagedenis* biotype Reiter, $2 \times 10^8$ cells per ml in PBS; *H. ducreyi*, skim milk suspension of $5 \times 10^8$ CFU/ml in PBS: *N. gonorrhoeae*, $1 \times 10^9$ cells per ml in PBS; herpes simplex virus type 2, skim milk suspension of $1 \times 10^8$ PFU/ml in PBS; and normal rabbit testicular antigens.

Fixation was accomplished by allowing the samples to air dry for 30 minutes. Filter strips with antigens were presoaked for 30 to 60 minutes at 4° C. in PBS containing 4% (vol/vol) fetal bovine serum and 0.2% bovine serum albumin (Sigma Chemical Co., St. Louis, Mo.; radioimmunoassay grade). Strips were then exposed to the primary monoclonal antibody by moving strips to tubes containing either 8 ml of fresh presoak buffer mixed with 4 ml of a 3- to 4 day-old hybridoma clone supernatant containing anti-*T. pallidum* monoclonal antibody or 10 ml of fresh presoak buffer supplemented with 20 ug of affinity-purified anti-*T. pallidum* monoclonal antibody per ml. Tubes were rocked for 3 hours at 4° C., and unbound monoclonal antibody was removed by washing the strips four times in successive 10-ml portions of PBS plus 4% fetal bovine serum (rocking for 30 minutes at 4° C. for each wash).

To probe for binding of monoclonal antibody to respective antigens, strips were moved to tubes containing 12 ml of PBS plus 4% fetal bovine serum supplemented with $1 \times 10^6$ CPM of freshly $^{125}$I-labeled affinity-purified rabbit anti-mouse immunoglobulin G (IgG) (heavy and light chain specific) (specific activity of ca. $2.2 \times 10^7$ CPM/ug). Tubes were rocked gently overnight at 4° C. Excess $^{125}$I probe was removed by washing the strips four successive times in 12-ml portions of PBS (30 minutes at 4° C. for each wash). Strips were then removed, air dried, mounted on cardboard, and exposed to Fuji X-ray film with an enhancing screen (Kodak Cronex Lightening Plus) from 2 hours to 4 days for autoradiographic analysis of monoclonal antibody reactivity with antigens.

E. Western blots of treponemal proteins

*T. pallidum* was purified by the Percoll density gradient method of Hanff and colleagues (P. A. Hanff. S. J. Norris, M. A. Lovett, and J. N. Miller, 11 *Sex. Trans. Dis.* 275–286, (1984). After density gradient centrifugation, treponemes were washed free of Percoll by suspending the cells in PBS, followed by centrifugation at $13,500 \times$ g for 5 minutes This step was repeated several times to ensure that the organisms were free of Percoll.

Treponemas were suspended in 1 ml of PBS and sonicated on ice for 1 to 5 minutes with a microtip at a 50% pulse with a Branson model 350 sonicator at a setting of 4 to 5. The 1-ml sonicate was diluted with 0.5 ml of digestion buffer composed of 0.1875 M Tris-hydrochloride (pH 6.8), 30% (vol/vol) glycerol, 6% (wt/vol) sodium dodecyl sulfate and 0.25% (wt/vol) bromophenol blue as tracking dye. As a modified Laemmli procedure, the sonicate suspension was solubilized and reduced by boiling for 5 minutes in the presence of 5% (vol/vol) 2-mercaptoethanol before loading onto sodium dodecyl sulfatepolyacrylamide gels and subsequent electrophoresis. Gels with molecular weight markers were fixed and stained with 0.1% Coomassie brilliant blue.

Electrophoretic transfer of proteins to nitrocellulose paper was effected by a modification of the Western blot methods using a Trans-blot apparatus (Bio-Rad Laboratories, Richmond, Calif.). After a 5- to 10-minute equilibration period in blotting buffer (20 mM Tris base, 150 mM glycine, and 20% methanol), polyacrylamide gels were placed on wet filter paper (Whatman no. 1), and strips of nitrocellulose (Bio-Rad 0.45 um) were layered over the individual lanes. A second piece of filter paper was layered over the nitrocellulose, and the sandwich was placed between supports and loaded into the Trans-blot apparatus with nitrocellulose facing the anode. The chamber was filled with blotting buffer, and a voltage gradient of 8 to 10 V/cm was applied for 16 hours at 4° C.

Specific immunological detection of antigens was employed. Nitrocellulose strips were incubated in 20 ug of primary antibody (murine anti-*T. pallidum* monoclonal antibody) per ml in PBS plus 0.05% Tween 20 for 1 to 3 hours. The strips were then washed twice in PBS plus Tween 20 for 10 minutes. For detection of bound monoclonal antibody, the strips were incubated for 1 h in a $10^{-3}$ dilution of horseradish peroxidase-conjugated goat antimouse IgG (CA. 2 ug/ml final concentration) (Cappel Laboratories, Cochranville, Pa.). Excess antibody was removed from the strips by washing four times thoroughly in PBS plus Tween 20. The strips were rinsed in distilled water and developed with one part of a 3 mg/ml solution of 4-chloro-1-napthol (Sigma) in methanol mixed with five parts of 200 mM sodium chloride plus 10 mM Tris-hydrochloride (pH 7.2). Hydrogen peroxide was added to a final concentration of 0.01% and the strips were immersed in this solution for 10 minutes. As purple bands appeared, the strips were placed in a solution of 0.1% sodium azide to inhibit the peroxidase reaction. The strips were then dried and mounted.

EXAMPLE I

A total of 11 different monoclonal antibodies [3G5; 4H7; 13C6; 13G10; 1F4; 3B5; 8G2; 9B12; 4A10-1; 4A10-7; and 5A3-2]were examined by immunoblot assay described above for their ability to detect decreasing levels of *T. pallidum* cells. All antibodies tested detected spots containing 100,000 and 10,000 treponemes. Five of these clones, 3G5, 4H7, 13C6, 13G10, and 8G2, reacted with as few as 1,000 *T. pallidum* cells. In this particular experiment, however, monoclonal antibody 8G2 produced a somewhat higher background binding level of reactivity to the filter than the other antibodies tested.

EXAMPLE II

This example compares the sensitivity testing of monoclonal antibody 11E3 with four of the five most sensitive antibodies (8G2, 1F4, 13C6, and 3G5) previously examined in Example I. The starting level of *T. pallidum* cells per spot was increased fivefold. All five antibodies tested by immunoblot assay reacted well with 500,000 and 50,000 treponemes, and the PBS negative control was clearly negative. Among these clones, only antibody, 13C6 reacted with fewer than 50,000 *T. pallidum* cells; as few as 500 treponemes could be reproducibly detected by antibody 13C6. The reactivity of antibody 13C6 with only 50 treponemes was not reproducible and was only observed occasionally.

EXAMPLE III

Due to the apparently increased ability of monoclonal antibody 13C6 to detect low levels of treponemes as compared with other monoclonal antibodies tested, antibody 13C6 was mixed in combination with other selected monoclonal antibodies. The antibody mixtures were reacted with *T. pallidum* cells in an attempt to assess whether selected combinations of monoclonal antibodies could significantly enhance the detection of even fewer treponemes. The reactivity of monoclonal antibody 13C6 was not significantly enhanced when reacted against *T. pallidum* in combination with antibodies 8G2, 3G5, and 9B12. Antibody 13C6 was essentially as reactive with *T. pallidum* when used alone or in combination. Similarly, monoclonal antibody 9B12 yielded no increase above its own signal when used in combination with 3G5. As in other cases, the PBS control was negative. The detection of as few as 500 *T. pallidum* cells by antibody 13C6 was reproducible.

EXAMPLE IV

An additional immunoblot assay using monoclonal antibodies selected on the basis of reactivities demonstrated in Examples I, II,and III was performed with a somewhat more selective dilution series of treponemes. The immunoblot assay using carefully diluted treponemes to accurately determine the limits of sensitivity for the various monoclonal antibodies showed that monoclonal antibody 11E3 was capable of detecting between 1,000 and 2,500 *T. pallidum* cells, even in the presence of some background binding to the filters. Monoclonal antibody 8G2 reacted with only 1,000 treponemes; the detection characteristics for monoclonal antibody 13C6 were similar to those of monoclonal antibody 8G2. As found in the previous Examples, prolonged exposure of the autoradiograms revealed that 13C6 was capable of detecting as few as 500 treponemes in this assay. Such prolonged incubation for autoradiography did not significantly increase the background, thereby allowing *T. pallidum* detection at this low level. Thus, provided that background in the test assay system could be kept to a minimum, monoclonal antibodies 11E3, 13C6, and 8G2 show extreme sensitivity in the ability to detect as few as 500 to 1,000 treponemes. The remaining antibodies tested, 3G5, 4H7, 13C8, 13G10, and 9B12, all revealed the presence of 2,500 *T. pallidum* cells; this was slightly reduced from those sensitivities exhibited by clones 11E3, 13C6 and 8G2.

EXAMPLE V

Several monoclonal antibodies preselected upon the basis of high sensitivity for *T. pallidum* detection were employed in Western blot assays to determine their respective binding to *T. pallidum* antigens. Antibodies 4H7, 8G2, 11E3, 3G5, 13C6, 13C8, 9B12 and 13G10 bound to similar antigens possessing apparent molecular weights of 47,000 (major band) to 48,000 (minor band). When tested in the Western blot or other immunoassays with equivalent amounts of *T. phagedenis* biotype Reiter cells, none of these monoclonal antibodies bound to Reiter antigens. Other studies by the Applicants have shown that the 47,000–48,000 dalton antigen of *T. pallidum* is an abundant, surface exposed immunogen of the organism which is common to several pathogenic Treponema subspecies but absent in the nonpathogen, *T. phagedenis* biotype Reiter (Marchitto et al., Monoclonal Antibody Analysis of Specific Antigenic Similarities Among Pathogenic *Treponema pallidum* Subspecies, *Infect. Immun.* 45:660-666 (1984); and Jones et al., Monoclonal Antibody With Hemagglutination, Immobilization, and Neutralization Activities Defines An Immunodominant, 47,000 Mol. Wt. Surface-Exposed Immunogen of *Treponema pallidum* (Nichols), *J. Exp. Med.* 160:1404-1420 (1984).) Anti-*T. pallidum* monoclonal antibodies directed against the 47,000–48,000 dalton surface immunogen of *T. pallidum* have proved to possess the high-est degree of sensitivity for the detection of *T. pallidum* cells and antigens. This is consistent with previous conclusions that the 47,000–48,000 dalton immunogen of *T. pallidum* may be one of the most abundant immunodominant antigens on the surface of virulent treponemal organisms (Ibid.).

EXAMPLE VI

In a survey experiment, 11 *T. pallidum*-specific monoclonal antibodies were reacted with various genital ulcerproducing sexually transmitted pathogens to examine their cross-reactivity with these organisms. At this time, clone 4A10-7 terminated its production of monoclonal antibody and therefore served as a negative control along with a control of PBS. All monoclonal antibodies tested [3G5; 4H7; 13C8; 13G10; 1F4; 3B5; 8G2; 9B12; 4A10-1; 5A3-2]bound to purified *T. pallidum*. *T. pallidum* cells freshly isolated from intradermal primary lesions of rabbits and suspended in a heavy background of the tissue exudate also yielded positive signals. All antibodies tested failed to react with the nonpathogenic Reiter treponeme, a clinical isolate of *H. ducreyi*, as well as with an extract of normal rabbit testicular material. Subsequent immunoblot experiments also have shown that these monoclonal antibodies do not react with the other nonpathogenic treponemes: *T. vincentii. T. denticola, T. refringens*, and *T. scoliodontum*. With the possible minor exception of monoclonal antibody 13C8, each of the antibodies also failed to react with herpes simplex virus type 2 and *N. gonorrhoeae*. These results indicated a high degree of specificity of the monoclonal antibodies for *T. pallidum*.

EXAMPLE VII

When monoclonal antibody 13C6 was tested in a similar assay for reactivity with these sexually transmitted pathogens, minor cross-reactivity with the N. gonorrhoeae and normal rabbit tissue preparations was observed.

MONOCLONAL ANTIBODY DEPOSIT

A deposit of hybrid cell lines which produce monoclonal antibodies identified herein as 3G5 (TPI-reactive) and 8G2 (MHA-TP-reactive) are on deposit with the American Type Culture Collection and assigned the ATCC numbers HB8133 and HB8134, respectively.

ALTERNATIVE IMMUNOASSAYS

Although the immunoblot assay described herein is operable and gives good results, this method employing radioisotope probes does not reflect the method of choice for routine diagnostic procedures in the clinical setting. Problems associated with radioactive probes such as environmental safety hazards and disposal problems preclude its overall usefulness.

The anti-*T. pallidum* monoclonal antibodies can be used in one or more of other many ways as a diagnostic test. In particular, the monoclonal antibodies can be tagged by conventional techniques with tracers such as radioisotopes, fluorescent labels, or enzymes. Such tagged antibodies are extremely useful in diagnostic tests. Various approaches can be utilized including both direct and indirect immunoassays. Variations on the general immunoassay theme include radioimmunoassay (direct or indirect), fluorescent antibody techniques (direct or indirect), enzyme-linked immunosorbent assays (ELISA's), inhibition of hemolysis assays, inhibition of agglutination tests, agglutination reactions (antibody-ligand mediated), and/or complement consumption tests. The use of one or more anti-*T. pallidum* monoclonal antibodies in such systems constitute an important new and useful test for the diagnosis of early primary syphilis, because the monoclonal antibodies are specific for *T. pallidum* and can be employed in very sensitive types of immunoassays. Such sensitive assays are also useful in the diagnosis of congenital syphilis or neurosyphilis through the detection of *T. pallidum* cells or antigens (pieces of cells or shedded material) in congenital syphilitic lesions or in the cerebrospinal fluid of neurosyphilitics.

The following summarizes those procedures that can be utilized with monoclonal antibodies in constructing immunologically specific assays for *T. pallidum*. A spectrum of technologies is presented to point out the breadth of visualization ("reporting") procedures that can be used to determine the presence of a specific interaction between a monoclonal antibody and the antigen (epitope bearing entity) for which it has affinity.
I. Primary assay methods: Partition based methods.

1. Radioactivity Exogenously labelled antibody Endogenously labelled antibody
2. Fluorescence: visual scan; patterning
3. Agglutination
4. Complement fixation
5. Enzyme enhanced procedures II. Secondary or indirect assay methods. Also, partition based methods.
   1. Anti light chain and heavy chain
   2. Anti idiotype
   3. Hapten based methods
   4. Other Lectin based methods
   5. Avidin/Biotin III. Radioimmunoassay based methods: Displacement or competition methods.
   1. Radioactivity
   2. Enzyme based/colorimetric
   3. Exotic methods
      a. Chemiluminisence
      b. FAD - Antigen
      c. Electrochemical
      d. Metalloimmunoassay Importance of Partition. Most assay procedures of any sensitivity rely on (1) association between antigen (Ag) and antibody (Ab), (2) subsequent partitioning between the reacted and unreacted materials, and (3) final measurement of Ab-Ag complex or loss of free Ag or loss of free Ab, one of which is "marked" in some way. This partitioning process can be simple, such as the binding of antibody to a surface bearing the antigen (transition from solution phase to solid phase with subsequent change of state and concentration). More complex procedures require additional physical treatments to partition antibody from unreacted antigen (for example, "salting out" of antibody but not soluble antigen). Not all strategies are equally effective and must be chosen with care and with regard to the physical and chemical properties of both the antigen and the antibody.

In the particular setting of detection of Treponema, we are trying to detect a small particle. Thus, suspensions can be treated as if homogenous solution or partition can be affected by as simple a procedure as washing by centrifugation. A further advantage is evident, since this microorganism is of sufficient size to be visualized, and because of the unusual "cork screw" shape of the organism, visual discrimination can be used as an additional procedure. For instance, if visual fluorescence is used as a detection method, not only will detection be based on a threshold amount of material emitting light of a given color, but the pattern of the distribution of that light emitting material will serve as a useful guide for the determination of the presence of an authentic *Treponema pallidum* organism.

I. PRIMARY ASSAY METHODS

(1) Radioactivity Procedures for "Marking" of the Antibody

Exogenously labelled antibody. Because of hybridoma technology, the antibody is available in large quantities for chemical modification with a radioactive element such as $I^{125}$, $I^{129}$, $H^3$, $C^{14}$, or $S^{35}$. These modifications can be direct such as the iodination of tyrosine residues or indirect such as chemical modification of amino groups by an active molecule (such as a sulfonyl chloride derivative that bears a radioactive element $S^{35}$, $H^3$, or $C^{14}$).

After partitioning between antigen and radioactive antibody, the antigen containing fraction is tested for retention of label. Several methodologies can be employed of varying sensitivity. Radioautography will detect all of the above isotopes. This is a sensitive procedure but requires considerable time.

Scintillation counting with solid phase crystals are useful with $I^{125}$, $I^{129}$ but not $C^{14}H^3$ or $S^{35}$. These latter elements are best detected using liquid scintillation counting.

Biosynthetic labelling of the antibody. Because the antibody is made by in vitro cell lines, it is possible to biosynthetically label the antibody. The cell line is grown in tissue culture media with no methionine, and the media is supplemented with $(S)^{35}L$-methionine of a very high specific activity. The antibody made is thus intrinsically labelled. This procedure has the advantage that no chemical modification need be performed and thus no loss of immunologic activity is expected.

Detection or binding is as described above. With intrinsic labelling, it is not possible to use $I^{125}$ or $I^{129}$.

Overall uses of Radioactive Methods

Advantages. Very "hot" molecules can be prepared and a very sensitive technology created.

Disadvantages. (1) Potential loss of biological activity when antibody is chemically modified. (2) Hazards associated with working with radioactive isotopes, e.g., exposure to ionizing radiation.

A Typical (Possible) Suggested procedure as an Example:
1. Sample "fixed" onto glass slide by physical attachment or by using a monoclonal "capture" procedure.
2. Exposed to $S^{35}$ methionine intrinsically labelled antibody.
3. Wash away unbound antibody (partitioning).
4. "Dipping" of slide into photographic emulsion.
5. Accumulation of exposure (1-3 days).
6. Development and scanning of slide looking for:
   a. accumulation of silver grains;
   b. pattern of silver grains - ought to be linear and cork screw-like.

(2) Fluorescence Methods

In these methods the antibody is coupled with an agent that emits light of a distinctive wave length after exposure to light of lower wave length. For example, the often used fluorescein which fluoresces green on exposure to blue light.

This method also has the advantages that the shape of the spirochete is a helpful identifier when visual observation is used. Disadvantages are that chemical modification of the antibody molecule is required. Sensitivity varies with the nature of the fluorphore, phycoerythrin being the most sensitive. The technology for visual scanning is widely available for fluorescein and less readily available for exotic fluorphores such as Texas red. This latter exotic dye is useful when used in conjunction with a second reagent that has a fluorphore that emits light of a different color. Thus, the presence of more than one epitope can be ascertained simultaneously. The chemical modification technology is broadly available. Fluorescein derivatives of the anti-Treponema monoclonals have been prepared and their utility in detecting *T. pallidum* reported (S. A. Lukehart et al. J. Immunol. 134:585-592 (1985)). Again, a proposed procedure would be:

1. Fixation of antigen (acetone slide) (a variety of procedures could be used).
2. Exposure to fluorophore-antibody conjugates.
3. Washing (partitioning) away excess, unreacted probe.
4. Visual observation with fluorescent microscope for green emitting organisms of appropriate size and shape.

(3) Agglutination

Monoclonal antibodies can be used most readily to agglutinate particles by setting up a "capture" system. For such an assay to be effective, two monoclonal antibodies reacting with two distinct epitopes of the *T. pallidum* are necessary. The "capture" antibody is placed on a particle (e.g., latex) by chemical means. The antibody-loaded particles are mixed with antigen bearing material/media and the antigen is bound to the surface of the particle and washed free of excess or unrelated material. The particle-Ab-Ag complex is now reacted with free antibody molecules of the second specificity which links together the particles. Aggregation of particles is read as a positive reaction. Because the *Treponema pallidum* organism will have a very high density of epitopes per organism and a small number of organisms, the concentration of antigen may be quite low. To enhance the availability of antigen, a mild detergent could be added to the sample that would not block the Ab-Ag reaction but would effectively "solubilize" the antigen-bearing molecule overall increasing the concentration greatly.

Because of the above unproven but logical approaches to the utilization of the antibodies in an agglutination assay, the procedure has a relatively low priority. In favor of such procedures is the extreme simplicity of the readout system for the assay as well as the comparable safety of the procedure and accessibility to unskilled lab workers.

(4) Complement Fixation

In principle, this procedure can detect any antibody-antigen reaction that consumes complement added to the reaction mixture. In the case of use for clinical samples with monoclonal antibodies, the chances that this procedure will be a preferred embodiment are slim for the following reasons:

(a) Complement fixation requires an antibody of the appropriate class that fixes complement at high efficiency (some of the antibodies in our panel are satisfactory but others are not).

(b) For efficient complement fixation, two antibodies of an appropriate class must be adjacent. But monoclonal antibodies are expected to be specific for only one epitope per molecule of antigen thus nearby interactions are not expected unless the entity being measured is highly polyvalent with multiple, closely situated determinants. This may be true for the 47-48K antigen of *T. pallidum* since certain monoclonal antibodies do fix complement. Thus, this might be true for detection of the whole Treponema organism or fragments, but there are uncertainties.

(c) The complement consumed is related to the number of antibody-antigen reactions taking place and since complement detection is not a sensitive method, small amounts of complement "consumed" must be assayed. Such measurements are difficult and subject to artifacts.

(d) Complement measurement is time consuming and difficult to perform in a quantitative, reliable fashion under the range of conditions expected in a clinical laboratory setting.

(5) Enzyme Enhanced Procedures

This set of approaches use constructs of monoclonal antibodies and enzymes that react with low molecular weight substrates to produce colored products (either soluble or insoluble), or soluble fluorescent molecules. Again, the procedure depends upon partition of antigen-antibody-enzyme complex from antibody-enzyme so that enzyme activity marks the presence of antibody.

The possible embodiments are many: when coupled to capture methods, one can create a large matrix of possible combinations of detection procedures and partition procedures. As one example, a capture monoclonal is placed on a solid matrix (filter paper). The fluid containing the antigen is placed with the filter paper and the antigen binds to the paper. The unbound material is then washed away. Next, the enzyme-conjugated monoclonal antibody (reacting with a different epitope on the same antigen) is added and incubated. Now the enzyme-Ab conjugate becomes bound to the filter paper and any excess is washed away. Finally a solution of substrate (for the enzyme) is added and the reaction allowed to proceed. The longer the incubation period, the more sensitive the detection (if the signal to noise ratio is sufficient). At the end of the reaction, the fluid is removed and measured or measured in the reaction vessel. If the product is colored and insoluble (formazans) the positive reaction will appear as a colored spot. If the reaction product is colored and soluble, an absorbance measurement is performed. If the product is fluorescent, a fluorescence measurement is performed. The most sensitive method is the latter and the least sensitive, the first. Success depends on the specificity of the reaction (monoclonal), the non-specific interactions present (signal to noise) and the ability to detect the product.

Simpler partition methods might include fixing the clinical material to a slide, and detection of enzyme product by microscopic examination. The solid support could also be the reaction vessel walls or particles added to the reaction vessel.

Enzymes that have been used so far with such procedures include as commercially available conjugates:
1. Peroxidase
2. Alkaline phosphatase
3. B-galactosidase
4. Glucose oxidase
5. Acetylcholinesterase Some of these enzymes are more sensitive because they have higher turnover numbers and thus create more reaction product per bound molecule per unit of time. Others have the advantage that the activity is not mammalian (e.g., glucose oxidase) and thus will not be present in clinical samples. This will lower possible sources of error in the assay procedures.

Reaction products include insoluble material (horeradish peroxidase), fluorescent products (B-galactosidase) and soluble colored products (alkaline phosphatase).

It is in the range of these possible systems that we feel the best methods for antigen detection are obtained. The most convenient would be colored spots on paper. However, equally useful but requiring more equipment would be colorimetric detection methods. Best, but the most trouble in terms of equipment cost, would be methods based on detection of fluorescent products.

II. SECONDARY OR INDIRECT ASSAY METHODS

The partition of the antibody-antigen system where the antigen is in the fixed phase, allows the introduction of a new strategy. The first antibody attached to the solid phase antigen introduces a new molecule. Because of its specificity for the antigen, the number of the antibodies is directly proportional to the amount of antigen and measurement of the first antibody will be at least as sensitive as measurement of the antigen. The secondary methods that are likely to be of some value are those that detect the first antibody used as a unique entity in the reaction mixture after partition. We will describe situations where this strategy can be used.

(1) Anti mouse light chain

The system may consist of a murine monoclonal antibody attached to a solid phase antigen (*T. pallidum*). An antibody, of the conventional type or monoclonal, specific for the murine light chain of immunoglobulin and not reactive with human light chains of immunoglobulin, can be used as the "second" antibody to detect the mouse antibody and hence the *T. pallidum*. This secondary antibody can be used with any of the detection systems employed by the primary detection system with the usual and appropriate caveats. This anti light chain reagent, usually described as anti mouse kappa, can be used with almost any murine monoclonal since they almost always have light chains of the kappa type.

A similar reagent that would be useful is a conventional or monoclonal antibody reactive with a class of murine antibody, which was also not reactive with human immunoglobulin. This type of reagent would be less useful since the primary could be of any of several subclasses of murine IgG or it could be of a different class such as IgM or IgA. Thus, only certain secondary sera and primary monoclonals could be used together. Again detection systems span the range mentioned in Section I.

(2) Anti idiotype

A potentially very useful reagent would be a secondary agent that reacted only with the particular monoclonal antibody used as the primary. Such a secondary could be based on the specificity of the primary and would be an "anti-idiotypic" reagent. It is possible to raise such reagents and even monoclonals have been prepared. The potential drawback of such secondaries is their reactivity with the same part of the immunoglobulin that reacts with the antigen, i.e., the "active site". Anti idiotypes that compete with antigen are not useful. However, according to the network theory of Jerne, other idiotopes exists on antibodies and are not at the antigen binding site. Such sites are "idiotypic" but not antigen binding. Anti idiotype directed to these "idiotopes" would be ideal secondary reagents. Such anti-idiotypes have been described but not used as secondaries in tests for antigen. However, nothing known precludes their use as a near ideal secondary reagent.

(3) Hapten Modification Methods

Another way of identifying the primary reagent unique to the reaction mixture is to chemically modify the primary reagent by introducing a new antigenic epitope. This is conventionally accomplished by introducing the Azobenzenearsonate (ARS) or 2,4,6-trinitrophenyl- (TNP) or one of several other epitopes. Such chemical species are not likely to be adventitious in the reaction mixtures and thus uniquely mark the primary reagent. These new chemical species are identified by reaction with a secondary antibody reactive with that group, for instance ARS- modified primary is reacted after partition with monoclonal (or conventional) anti ARS antibody marked with any of the previously mentioned detection systems. Such anti-hapten monoclonals are readily and freely available, we have prepared several (Robertson et al. Federation Proceeding 41(9):2502-2506 (1982)). This technology is superior to the above anti idiotype strategy in that while only the chemically modified primary is measured or detected in the reaction system, the secondary reagent (anti ARS in this case) can be used with any primary (so chemically modified) while an anti idiotype can be used only with that one monoclonal for which it is specific. This flexibility is convenient.

(4) Lectin Modifications:

Similar to the above anti-hapten methods are chemical modifications that introduce into the primary reagent, a new molecule that binds specifically to a plant lectin. The plant lectin is in turn chemically modified so as to be detected. Such procedures have been proposed and used rarely so far. One potential drawback is that the lectin used should not bind to any other molecule present in the reaction mixture after partition. For carbohydrate groups introduced onto the primary, the condition may or may not be met, only clinical testing can ascertain if the lectin "epitope" being detected is found in the range of material found in the clinic and if it is, it will introduce too high a number of false positives.

(5) Biotin-Avidin

There is one molecule widely used as ligand with which much experience is available as well as the chemical technology. Biotin can be introduced onto the primary monoclonal antibody creating a unique entity reactive with avidin or streptavidin. The system has found wide acceptability and utility and our system can be modified to use this procedure. The avidin is modified to be detected as are the primary monoclonal antibodies described in I.

III. RADIOIMMUNOASSAY METHODS: DISPLACEMENT OR COMPETITION METHODS.

In addition to direct measurement or detection systems, indirect displacement methods are widely used for measurement of biological materials where precise measurements are desirable. In such situations, the antigen is labelled with a marker and reacted in limiting amounts with the antibody directed against an epitope of the antigen. The system is allowed to reach equilibrium and then partitioned. The amount of antigen bound is measured by measuring the marker. To be used for unknown material, the system is standardized by the addition of known amounts of unmarked antigen. The introduced material then competes for the antibody binding site with the labelled material. Because the amount of antibody is fixed, the marked antigen is effectively diluted and less marker is present in the partitioned antibody-antigen complex. Thus, a standard curve is constructed based on the amount of unmarked antigen introduced and the loss of marked antigen found with the antibody.

In the context of detection of the presence of *Treponema pallidum* antigens, the purified antigen, specific for pathogenic Treponema will be marked by one of the methods listed below. Using monoclonal antibody fixed to a plastic surface (the sides of the plastic reaction vessel), the marked antigen, as well as the unmarked antigen, a titration curve will be constructed. This will establish the sensitivity of the method. The clinical sample will be introduced into the reaction vessel and bind to the monoclonal antibody fixed to the wall, occupying antibody sites. After washing away excess material, the marked antigen will now be introduced and reacted. Again, the system will be partitioned. Finally, the amount of marker present stuck to the vessel walls will be determined by the methods mentioned below.

The methods should be sensitive and specific and readily adaptable to kit procedure. The strategy of construction is different from the above methodologies since the antigen is now marked and measured rather than the antibody. Outside of the affinity, the properties of the antibody are unimportant. This is different from the methods listed in I and II where the properties of the antibody were essential as well as the origin of the biological specificity of the system.

Further, since it is possible to determine the sequence of the epitope recognized by the antibody (by recombinant DNA tecnology, gene cloning, and sequence analysis as well as conventional analytical procedures), it may be possible to synthesize the probe used for the marked antigen in these systems.

It is clear that the antigen must be marked and thus available in reasonable quantities. Since immunoprecipitation of the very abundant, relevant antigen on Treponema is possible, suitable amounts of antigens should be available by conventional procedures as well as the recombinant technologies mentioned above.

Marking of the antigen

The antigen could be the entire molecule, e.g., principle membrane protein of the *T. pallidum,* or some fragment isolated or synthesized which reacts with the antibody to a reasonable extent (full reactivity is not essential).

(1) Radioactivity $I^{125}$, $I^{129}$, $H^3$, $C^{14}$ or $S^{35}$ would be introduced by chemical modification of isolated materials or "built in" during synthesis of the relevant molecule (polypeptide). Detection would depend on the isotope and the desired sensitivity of the assay. Presumably, scintillation or liquid scintillation counting would be the preferred manifestation. The properties of this technology are as discussed earlier.

(2) Enzyme linked methods

As discussed in detail earlier, coupling of the antigen to an enzyme allows a large variety of different assays dependent on properties of the enzyme and substrate used. Such methods would be especially convenient but would depend on some quantitative measurement of reaction product and each set of measurement would need to incorporate internal controls so that proper interpretation of the diminished amount of reaction product could be obtained.

(3) Exotic methods

Several exotic methods have been used in conjunction with this approach of antigen measurement. These include linking the antigen to luciferinase. With this assay, the amount of light emitted on reaction of the enzyme with substrate is measured by scintillation. Although "equipment-intensive", the methods avoid the hazards of ionizing radiation.

Another exotic method uses FAD (flavine adenine dinucleotide) coupled antigen. In this manifestation, antigen not coupled to the antibody (e.g., displaced by the free antigen), is used as a co-factor by glucose oxidase. In the presence of substrate, glucose oxidase, (made active by the displaced FAB-antigen), produces peroxide. This is detected by the enzyme peroxidase, which while consuming peroxide produced by the glucose oxidase produces a colored product that is the final measured entity.

Other exotic methods are fundamentally of the conventional sort and use antigen bound to a nitro group bearing molecule that can be electrochemically reduced and detected. Further, metal containing antigen complexes have been prepared and the bound metal ion detected by sensitive atomic absorption spectroscopy.

All of these exotic procedures seek to use new technologies that allow the accurate measurement of small amounts of material in highly specific fashions. There are probably many other manners of accomplishing these goals. All of these methods depend on the identification of the antigen, reaction with a specific antibody (here a monoclonal), prepared and deposited by us. Further, the antigen must be modified and marked without elimination of immunologic reactivity with the above monoclonals. Finally, a sensitive detection method of the marked molecule must be employed after the use of a partition method or procedure. There are several such possibilities for partition. We here prefer, but do not limit ourselves to "phase change" from solution to a solid surface such as the wall of the reaction vessel which would be used for the entire procedure, including final measurement.

The foregoing description of the invention has been directed to particular embodiments for purposes of explanation and illustration. It will be apparent, however, to those skilled in the art that many modifications and changes in the processes of preparing and implementing the described embodiments may be made without departing from the essence of the invention. It is Applicants' intention in the following claims to cover all equivalent modifications and variations as fall within the scope of the invention.

What is claimed is:

1. A method for diagnosing syphilis and treponematoses infection in a patient suspected of having syphilis comprising (a) providing a biological sample obtained from the patient;

(b) admixing the biological sample with a primary immunoreagent of monoclonal antibodies directed against an antigenic determinant of virulent subspecies of *Treponema pallidum,* said antibodies produced from a continuous murine hybrid cell line formed by fusing a murine myeloma cell with a differentiated murine lymphoid cell immunized against virulent subspecies of *Treponema pallidum* antigens; and (c) detecting a positive immunobinding reaction which indicates the presence of virulent subspecies of *T. pallidum*. the causative agent of syphilis and treponematoses.

2. The method of claim 1 wherein the biological sample comprises lesion exudate, cerebrospinal fluid, serum, urine, amniotic fluid, synovial fluid, or tissue homogenate.

3. The method of claim 1 wherein the primary immunoreagent consists essentially of monoclonal antibodies directed against a 47,000–48,000 dalton surface exposed antigen of *T. pallidum*.

4. The method of claim 1 wherein the immunoreagent consists essentially of monoclonal antibodies produced from the hybrid cell lines identified as ATCC deposit HB8133 or HB8134.

5. The method of claim 1 wherein the positive immunoreaction is detected by direct or indirect radioimmunoassay; direct or indirect fluorescent tagged antibody techniques; direct or indirect enzyme-linked immunosorbent assay; inhibition of hemolysis assay; inhibition agglutination assay; agglutination reactions; or complement consumption assay.

6. The method of claim 1 wherein the monoclonal antibodies are tagged with a radioisotope, a fluorescent label, or an enzyme.

7. The method of claim 1 wherein the monoclonal antibodies fail to react with nonpathogenic treponemes.

8. An immunoreagent for use in methods to detect syphilis and treponematoses infection consisting essentially of:
monoclonal antibodies directed against an antigenic determinant of virulent subspecies of *Treponema pallidum* labelled with a marker.

9. The immunoreagent of claim 8 wherein the monoclonal antibodies are tagged with a radioisotope, a fluorescent label, an enzyme, a lectin, avidin, biotin, a chemiluminescent tag, or flavine adenine dinucleotide.

10. The immunoreagent of claim 8 wherein the monoclonal antibodies are produced by the hybrid cells lines identified as ATCC deposit HB8133 or HB8134.

11. An immunoreagent for use in methods to detect syphilis and treponematoses infection consisting essectially of:
monoclonal antibodies directed against an antigenic determinant of virulent subspecies of *Treponema pallidum* in a fixed phase.

12. The immunoreagent of claim 11 wherein the monoclonal antibodies are fixed to a plastic reaction vessel, a glass slide, latex particles, or filter paper.

13. The immunoreagent of claim 11 wherein the monoclonal antibodies are produced by the hybrid cell lines identified as ATCC deposit HB8133 or HB8134.

* * * * *